(12) United States Patent
Saito

(10) Patent No.: US 9,510,750 B2
(45) Date of Patent: Dec. 6, 2016

(54) FUNDUS IMAGING APPARATUS, METHOD OF CONTROLLING FUNDUS IMAGING APPARATUS, AND STORAGE MEDIUM

(71) Applicant: CANON KABUSHIKI KAISHA, Tokyo (JP)

(72) Inventor: Kenichi Saito, Pittsford, NY (US)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/849,628

(22) Filed: Sep. 10, 2015

(65) Prior Publication Data

US 2015/0374229 A1 Dec. 31, 2015

Related U.S. Application Data

(63) Continuation of application No. 14/112,968, filed as application No. PCT/JP2012/061306 on Apr. 20, 2012, now abandoned.

(30) Foreign Application Priority Data

Apr. 27, 2011 (JP) .................. 2011-100136

(51) Int. Cl.
*A61B 3/14* (2006.01)
*A61B 3/10* (2006.01)
*A61B 3/12* (2006.01)
(52) U.S. Cl.
CPC .............. *A61B 3/1015* (2013.01); *A61B 3/12* (2013.01); *A61B 3/14* (2013.01)
(58) Field of Classification Search
CPC .............................. A61B 3/1015; A61B 3/112
USPC ......................... 351/206–210, 221
See application file for complete search history.

(56) References Cited

U.S. PATENT DOCUMENTS

| | | | |
|---|---|---|---|
| 7,281,797 B2 | 10/2007 | Yamaguchi et al. |
| 7,387,387 B2 | 6/2008 | Dai |
| 7,708,410 B2 | 5/2010 | Dai |
| 8,506,082 B2 | 8/2013 | Saito |
| 8,801,178 B2 | 8/2014 | Mukai et al. |
| 2002/0135736 A1 | 9/2002 | Stark et al. |
| 2005/0280777 A1 | 12/2005 | Dai |

(Continued)

FOREIGN PATENT DOCUMENTS

| | | |
|---|---|---|
| EP | 1 609 405 A1 | 12/2005 |
| JP | 2005-292662 A | 10/2005 |

(Continued)

OTHER PUBLICATIONS

Robert J. Zawadzki, et al., "Ultra-high-resolution optical coherence tomography with monochromatic and chromatic aberration correction", Optics Express, vol. 16, No. 11, May 2008, pp. 8126-8143.

(Continued)

*Primary Examiner* — Mahidere Sahle
(74) *Attorney, Agent, or Firm* — Fitzpatrick, Cella, Harper & Scinto

(57) ABSTRACT

A fundus imaging apparatus comprising: position detection means for detecting a position of a pupil of an eye to be examined; wavefront detection means for detecting a wavefront of return light from the eye irradiated with light through an illumination optical system; correction means for correcting an aberration based on the detected wavefront; and determination means for determining a correction effective region of the correction means based on the detected position.

13 Claims, 7 Drawing Sheets

(56) References Cited

U.S. PATENT DOCUMENTS

| | | |
|---|---|---|
| 2005/0286018 A1 | 12/2005 | Yamaguchi et al. |
| 2007/0252951 A1 | 11/2007 | Hammer et al. |
| 2008/0218693 A1 | 9/2008 | Dai |
| 2009/0073384 A1 | 3/2009 | Warden et al. |
| 2011/0001930 A1 | 1/2011 | Levecq |
| 2011/0242487 A1 | 10/2011 | Yuasa et al. |
| 2011/0249236 A1 | 10/2011 | Saito et al. |
| 2012/0113389 A1 | 5/2012 | Mukai et al. |
| 2012/0274904 A1 | 11/2012 | Saito et al. |
| 2013/0021576 A1 | 1/2013 | Saito |
| 2014/0160435 A1 | 6/2014 | Saito |

FOREIGN PATENT DOCUMENTS

| | | |
|---|---|---|
| JP | 2006-006362 A | 1/2006 |
| JP | 2008-503271 A | 2/2008 |
| JP | 2010-518932 A | 6/2010 |
| JP | 4510534 B2 | 7/2010 |
| WO | 2011/061896 A1 | 5/2011 |

OTHER PUBLICATIONS

"Eye Development and Aging", edited by Seiichi Mishima, et al., Ophthalmology Mook No. 38, Kanehara Co., Ltd., 1989, pp. 80-85.
Aug. 14, 2012 International Search Report and Written Opinion in International Patent Appln. No. PCT/JP2012/061306.

F I G. 7
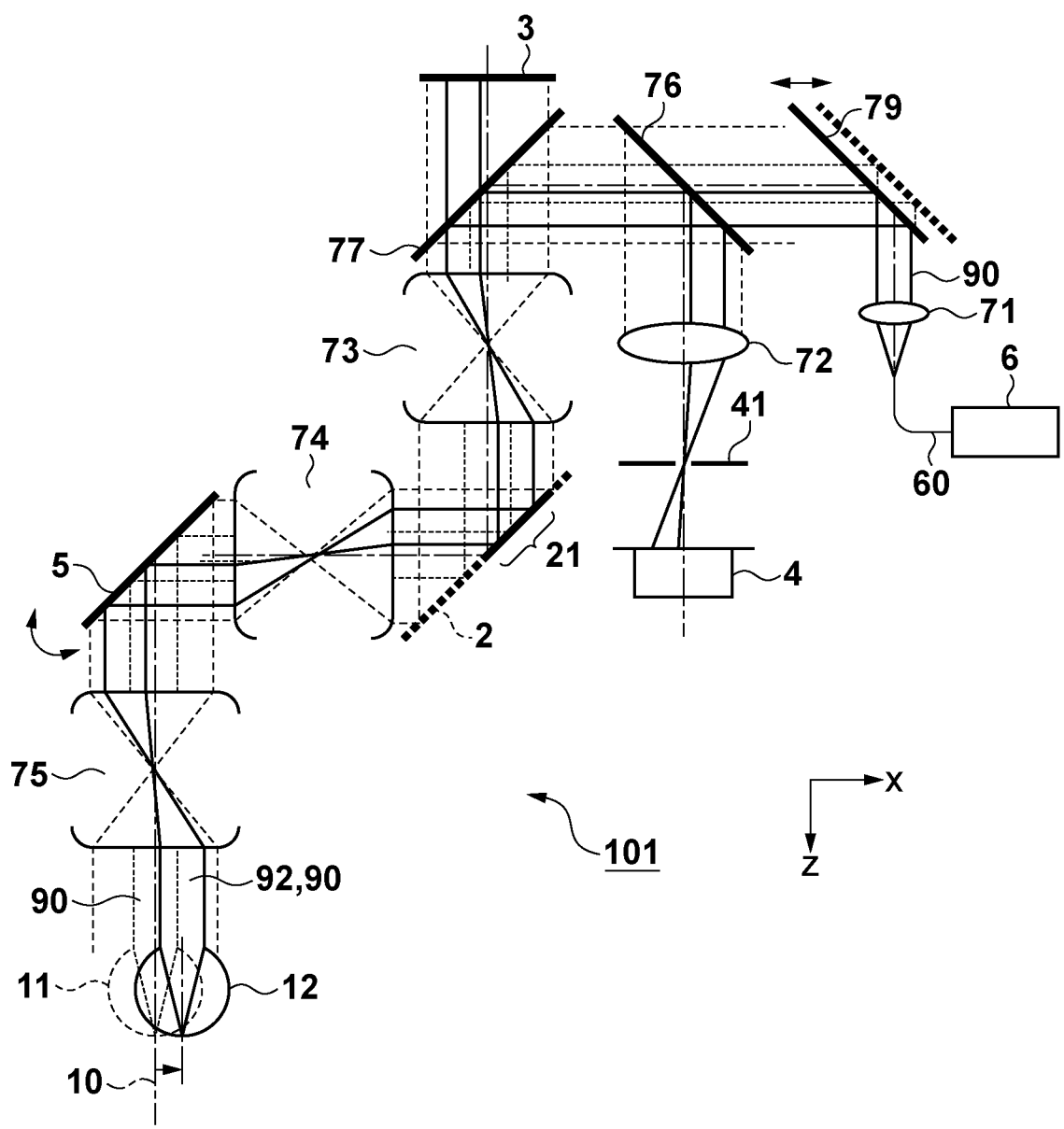

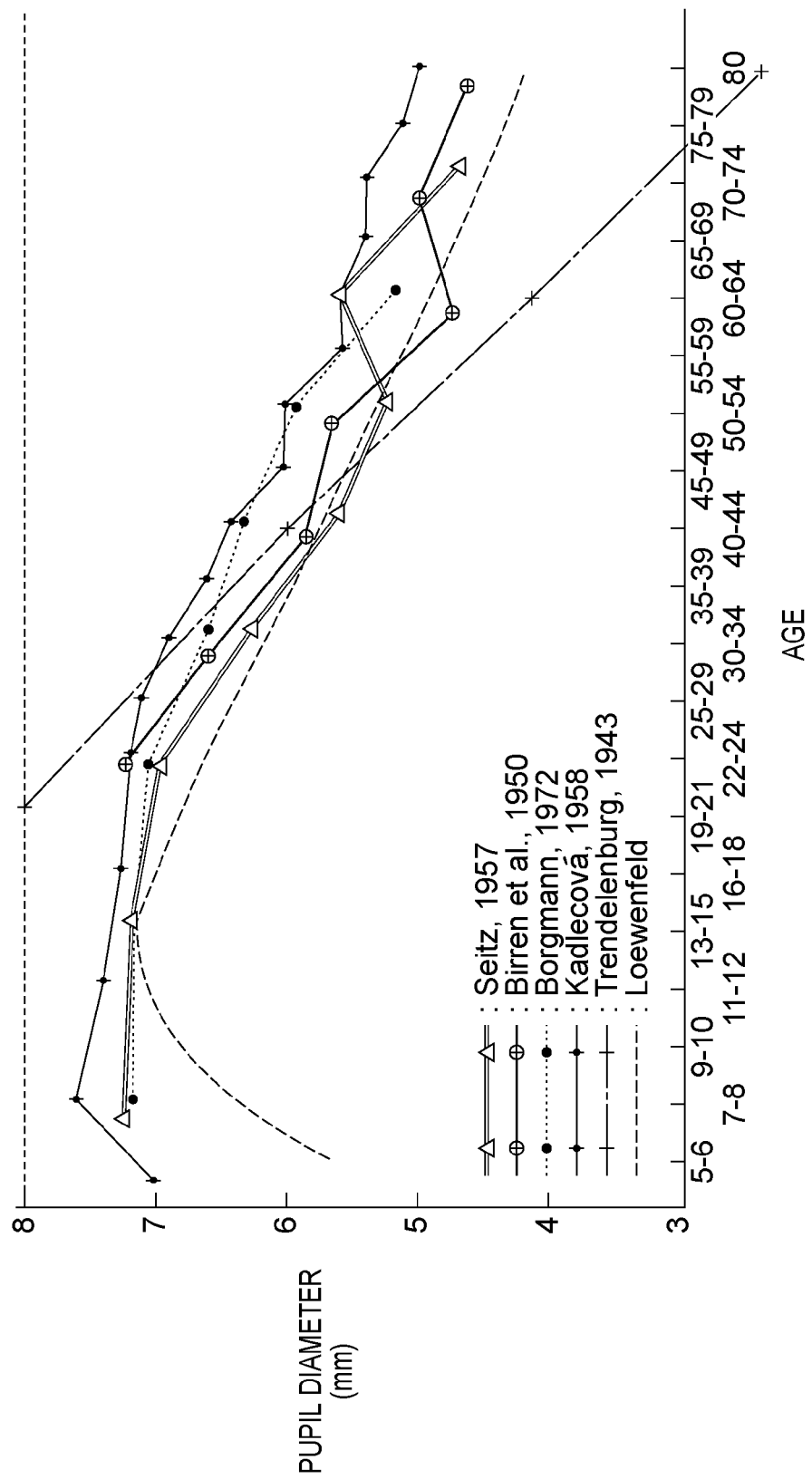

FUNDUS IMAGING APPARATUS, METHOD OF CONTROLLING FUNDUS IMAGING APPARATUS, AND STORAGE MEDIUM

This application is a continuation of application Ser. No. 14/112,968 filed Oct. 21, 2013, which was the National Stage of International Application No. PCT/JP2012/061306 filed Apr. 20, 2012.

TECHNICAL FIELD

The present invention relates to a fundus imaging apparatus, a method of controlling the fundus imaging apparatus, and a storage medium and, more particularly, to a fundus imaging apparatus having an adaptive optics function, a method of controlling the fundus imaging apparatus, and a storage medium.

BACKGROUND ART

As fundus imaging apparatuses designed to observe and capture two-dimensional front images and tomographic images of the retina of the eye to be examined, fundus camera, scanning laser ophthalmoscope (SLO), optical coherence tomography (OCT), and the like are well known and have long been in practical use.

These apparatuses are designed to obtain a retinal image by irradiating the retina as an imaging target with illumination light and by forming return light from the retina into an image on a light-receiving element or to obtain a tomographic image by interference with reference light. Light having a near-infrared wavelength is often used as this illumination light, which is not absorbed or scattered much by the light-transmitting living tissue (for example, the cornea, crystal lens, or corpus vitreum) in the eye to be examined.

The spatial resolution of an obtained image in the plane direction (lateral direction) of the retina (to be referred to as a "lateral resolution" hereinafter) is basically determined by the diameter of a beam spot scanned on the retina (or the numerical aperture of an optical system). In order to reduce the diameter of a beam spot focused on the retina, the light beam diameter of illumination light striking the eye to be examined (or the numerical aperture of the optical system) is increased.

The corner and crystal lens of the eye to be examined, which are mainly in charge of refracting light, are imperfect in terms of the uniformity of curved surface shape or refractive index. This causes high-order aberrations on the wavefront of light transmitted through these organs. For this reason, even if illumination light having a large light beam diameter is made to strike the retina, it is not possible to focus a spot on the retina at a desired diameter. Rather, the light beam diverges sometimes.

As a result, the lateral resolution of an obtained image decreases, and the S/N ratio of the image signal obtained by a confocal optical system also decreases. Conventionally, therefore, a thin beam having a size of about 1 mm, which is robust against the influence of aberrations of an optical system such as the cornea of the eye to be examined, is generally made to strike the retina to form a spot having a size of about 20 μm on the retina.

In order to solve such a problem, an adaptive optics technique is also being introduced to fundus imaging apparatuses. This technique is configured to sequentially measure the wavefront aberration of return light from a measurement target such as the eye due to variations in the characteristics of the target itself or measurement environment, and correct the aberration by using an active aberration correction device such as a deformable mirror or spatial light modulator. It was reported that making a thick beam having a size of about 7 mm strike the eye to be examined by using this technique can focus the beam into a spot diameter of about 3 μm, which is near the diffraction limit, on the retina by wavefront compensation, thus obtaining a high-resolution SLO or OCT image (see R. Zawadzki et al., "Ultrahigh-resolution optical coherence tomography with monochromatic and chromatic aberration correction" OPTICS EXPRESS/Vol. 16, No. 11/2008).

One major factor that makes it difficult to obtain stable images in a fundus imaging apparatus using adaptive optics is that the position of the pupil (iris) of the eye to be examined varies. This is caused because the head of an object to be examined moves back and forth and left and right, and the eyeball inevitably rotates in various ways in spite of the attempt to fix the line of sight by making the object observe a fixation lamp.

Using a bite bar can suppress variations in the position of the head, but will impose a burden on the object. For this reason, the use of a bite bar is not favorable sometimes. Furthermore, the ability to stably and continuously look at a fixation lamp varies among different individuals.

The first problem is that when the position of the head, that is, the position of the pupil of the eye to be examined, varies in a direction perpendicular to the optical axis of an eyepiece optical system, return light (reflected/backscattered light) from the retina also shifts on an aberration correction device placed at a position optically conjugate with the pupil. At this time, when wavefront feedback correction is performed in an open loop manner, since return light strikes the aberration correction device while shifting relative to the aberration correction value formed on the aberration correction device, the aberration correction residue increases, resulting in a deterioration in image quality, for example, a decrease in brightness or resolution.

The generation of an aberration correction value is generally expressed by the addition of function systems having orthogonality such as Zernike polynomials. In a closed-loop real-time aberration correction system as well, expressing this shift component will lead to a deterioration in the reproducibility of a curved surface unless using functions up to high-order functions. Limiting the number of orders for a reduction in calculation time makes it impossible to perform ideal aberration correction. This becomes a cause of the above deterioration in image quality.

Second, image obtaining illumination light is vignetted (limited). When, for example, a spot having a size of 3 μm is to be formed on the retina, it is necessary to make illumination light having a diameter of about 7 mm strike the pupil. In general, however, the diameter of the iris is about 8 mm even when it opens wide.

Assume that in this case, the head has moves by 1 mm to 2 mm with lapse of time. In this case, even if aberration correction is properly performed, the spot diameter on the retina increases to 4 to 5 μm to lead to a decrease in resolution. In addition, the amount of illumination light reaching the retina is lost by 10% to 20% due to vignetting. As a result, the brightness of the image also decreases.

Third, although the pupil of the eye to be examined, an aberration correction device, and a wavefront detector are arranged at optically conjugate positions with an afocal optical system, if return light falls outside the effective diameter of the optical system, even partly, the consistency of the wavefront at each position deteriorates. As a consequence, the feedback accuracy of aberration correction deteriorates. This leads to an increase in time for convergence or to divergence instead of convergence.

For the first problem, the following solution has been proposed in Japanese Patent No. 04510534. This technique provides a unit configured to observe the anterior ocular segment including the pupil to measure the position variation amount of the pupil in read time and to always match a correction effective region with the position of return light from the retina by following the position of the aberration correction device mounted on a mechanical stage in accordance with the calculated value.

However, this arrangement can solve the first problem but cannot solve the second problem. There is no mention about the third problem. In addition, since the aberration correction device generally has a volume of several $cm^3$ to 10 $cm^3$, the mechanical stage to be used inevitably has a large size, resulting in increases in the size and cost of the system. Furthermore, the vibrations of the stage may affect image quality.

SUMMARY OF INVENTION

In consideration of the above problems, the present invention provides a technique of performing aberration correction in accordance with the positional shift of the eye to be examined.

According to one aspect of the present invention, there is provided a fundus imaging apparatus comprising: position detection means for detecting a position of a pupil of an eye to be examined; wavefront detection means for detecting a wavefront of return light from the eye irradiated with light through an illumination optical system; correction means for correcting an aberration based on the detected wavefront; and determination means for determining a correction effective region of the correction means based on the detected position.

According to one aspect of the present invention, there is provided a method of controlling a fundus imaging apparatus, the method comprising: a position detection step of detecting a position of a pupil of an eye to be examined; a wavefront detection step of detecting a wavefront of return light from the eye irradiated with light through an illumination optical system; a control step of controlling correction means for correcting an aberration based on the detected wavefront; and a determination step of determining a correction effective region of the correction means based on the detected position.

Further features of the present invention will be apparent from the following description of exemplary embodiments with reference to the attached drawings.

BRIEF DESCRIPTION OF DRAWINGS

FIG. 7 is a view showing the arrangement of an SLO according to the second embodiment of the present invention;

FIG. 10 is a graph showing statistical data about pupil diameters.

DESCRIPTION OF EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
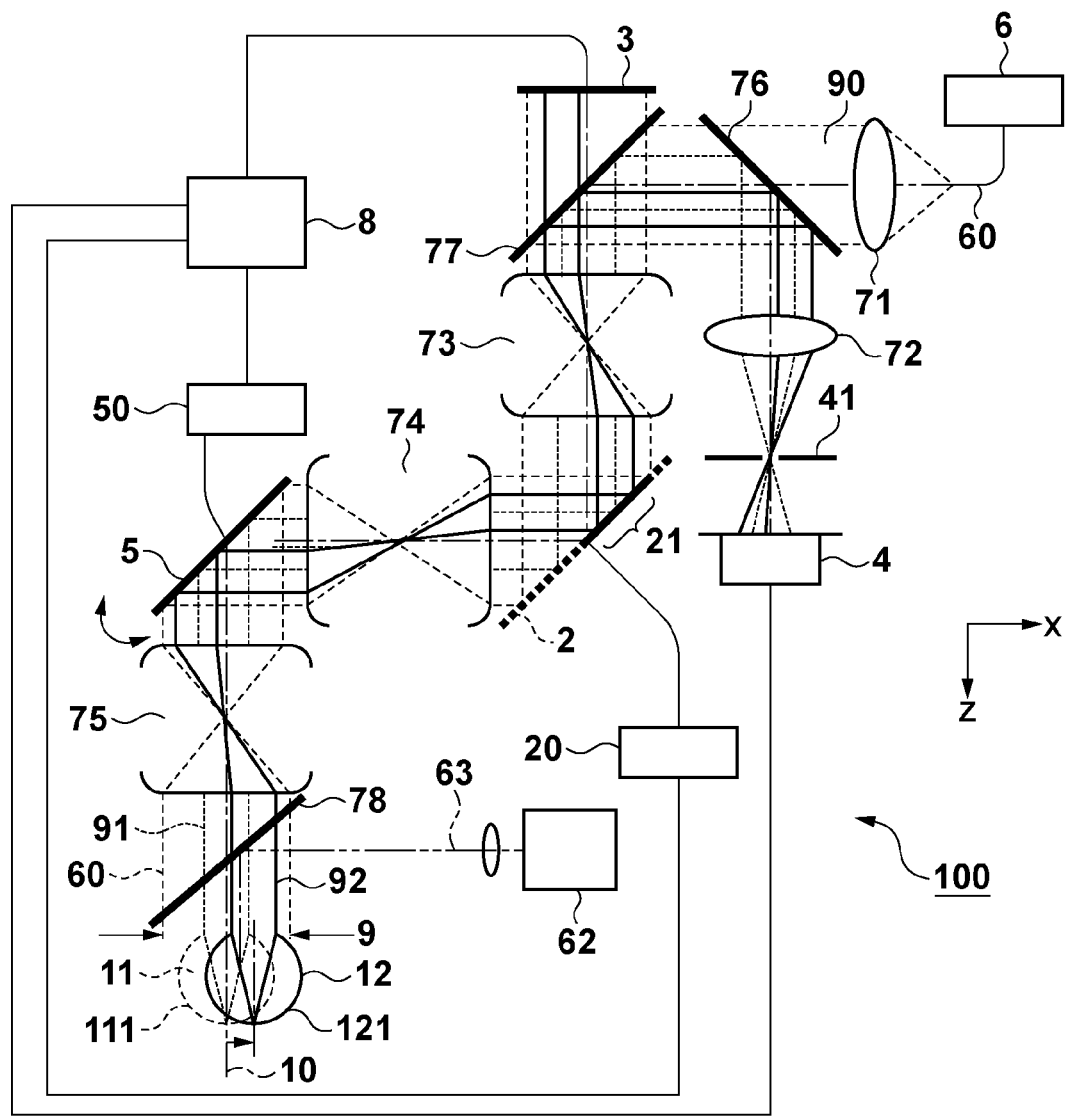
FIG. 1 is a view showing the arrangement of an SLO according to the first embodiment of the present invention.

The arrangement of a scanning laser ophthalmoscope (SLO) according to the first embodiment of the present invention will be described first with reference to FIG. 1. In an SLO 100, first of all, light from an image obtaining laser light source 6 propagates in a single-mode fiber 60 and emerges, as illumination light 90, from a fiber end. A collimator lens 71 converts the emerging illumination light 90 into parallel light (the broken lines indicate the marginal rays of the illumination light 90 and the effective diameter range of the optical system).

The illumination light 90 which has been converted into parallel light is transmitted through a half mirror 76, reflected by a first dichroic mirror 77, and reflected by an aberration correction device 2 through a first afocal optical system 73. The light then strikes a scanner mirror 5 through a second afocal optical system 74. An eyepiece optical system 75 causes the illumination light 90 reflected by the scanner mirror 5 to strike an eye 11 to be examined (indicated by the broken line), and focuses the light onto a retina 111.

In this case, an exit pupil 9 of the eyepiece optical system 75 and the light beam diameter of the illumination light 90 (the diameter of a region in which the intensity is $1/e^2$ (e is the base of a natural logarithm) the central intensity) are set to larger than the diameter of the pupil (pupil diameter) of the eye 11. Accordingly, the effective diameters of the first and second afocal optical systems 73 and 74, the collimator lens 71, and an imaging lens 72 are set to be larger than the diameter of the pupil (pupil diameter) of the eye 11. Although pupil diameters vary among individuals, according to the investigation example shown in FIG. 10 (see "Eye Development and Aging", edited by Seiichi Mishima et al., Ophthalmology MOOK No. 38, Kanehara Co., Ltd., 1989), the maximum pupil diameter is about 8 mm without using any mydriatic agent. Therefore, the value of the exit pupil 9 is set to be larger than at least this value. In this case, the diameter was set to 12 mm in consideration of the use of a mydriatic agent and the possible shift amount of the pupil of the eye 11.

In this case, the eye 11 is the eye to be examined when an optical axis 10 (chain line) of the optical system coincides with the center of the pupil. Return light 91 from the retina 111 of the eye 11 reversely propagates along the optical path of the illumination light 90 and is reflected by the half mirror 76. The light is then focused by an imaging lens 72, passes through a pinhole 41, and is detected by a photodetector 4. In this case, the marginal rays of the return light 91 are indicated by the dotted lines. A driver 50 drives the scanner mirror 5 to scan the illumination light 90 in a two-dimensional direction. A personal computer 8 then obtains a retinal image (fundus image) by synchronously capturing an electrical signal from the photodetector 4.

Wavefront detection light 63 (chain double-dashed line) generated from a light source 62 is reflected by a second dichroic mirror 78 and strikes the eye 11. The second dichroic mirror 78 has a transmittance near 100% with respect to the wavelength of the light source 6 and a transmittance of 50% with respect to the wavelength of the light source 62. The wavefront detection light 63 has a light beam diameter of 1 mm, and hence is hardly influenced by the aberration of the eye. Therefore, a spot diameter of about 20 μm is stably formed on the retina 111.

Return light of the wavefront detection light 63 from the retina 111 contains much scattered (diffused) light and has a spread, and hence emerges from the pupil of the eye 11 as a light beam having the same diameter as that of the pupil like the return light 91 of the illumination light 90. The light is transmitted through the second dichroic mirror 78, and is transmitted through the first dichroic mirror 77 through the optical systems 75 and 73. The wavefront of the light is detected by the detection region of a wavefront detector 3. The aberration correction device 2 corrects the wavefront aberration of the return light 91 by using the data detected and calculated at this time. Note that aberration correction may be performed for the illumination light 90 instead of the return light 91 or may be performed for both of them. Alternatively, this apparatus may be configured to detect a wavefront by using the image obtaining illumination light 90 without providing the light source 62 which generates the wavefront detection light 63.

The above arrangement properly forms the image obtaining illumination light 90 into an image on the retina 111 and also forms the return light 91 into an image at the pinhole 41, and hence can reduce the influence of the aberration of the eye 11 and stably obtain a bright, high-resolution image.

In this case, a deformable mirror is used as the aberration correction device 2, and a Hartmann-Shack detector (HS sensor) is used as the wavefront detector 3. The effective diameters (driving regions) of these detectors are 12 mm and 6 mm, respectively. The magnifications at these positions with respect to the exit pupil 9 of the optical system are respectively set to $\beta 2=12/12=1.0$ and $\beta 3=6/12=0.5$. If the pupil diameter of the retina 111 is 6 mm, the diameter of return light at the position of the exit pupil 9 is also 6 mm. Therefore, the diameters of the return light 91 at the aberration correction device 2 (deformable mirror 2) and the wavefront detector 3 (HS sensor 3) are respectively 6 mm and 3 mm.

The HS sensor 3 calculates the wavefront of light from the displacement of each point image formed on a two-dimensional imaging element by using each of microlenses arranged in a two-dimensional matrix. A set of these point images (HS images) are observed on the two-dimensional imaging element within a diameter range of 3 mm which corresponds to the pupil.

Figure 2:
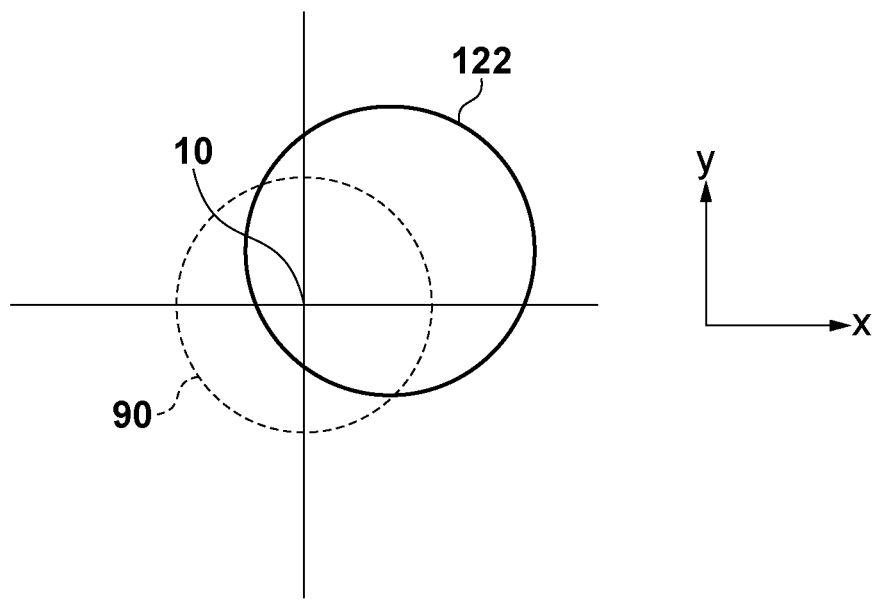
FIG. 2 is a view showing the positional relationship between the pupil of the eye to be examined and illumination light.
Figure 3:
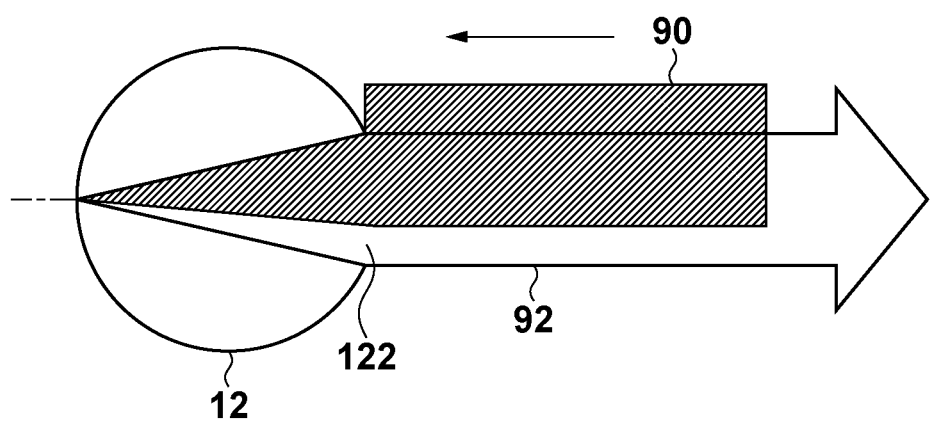
FIG. 3 is a view showing the positional relationship between illumination light and return light from the eye to be examined.
Figure 3:
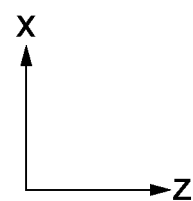
Figure 4:
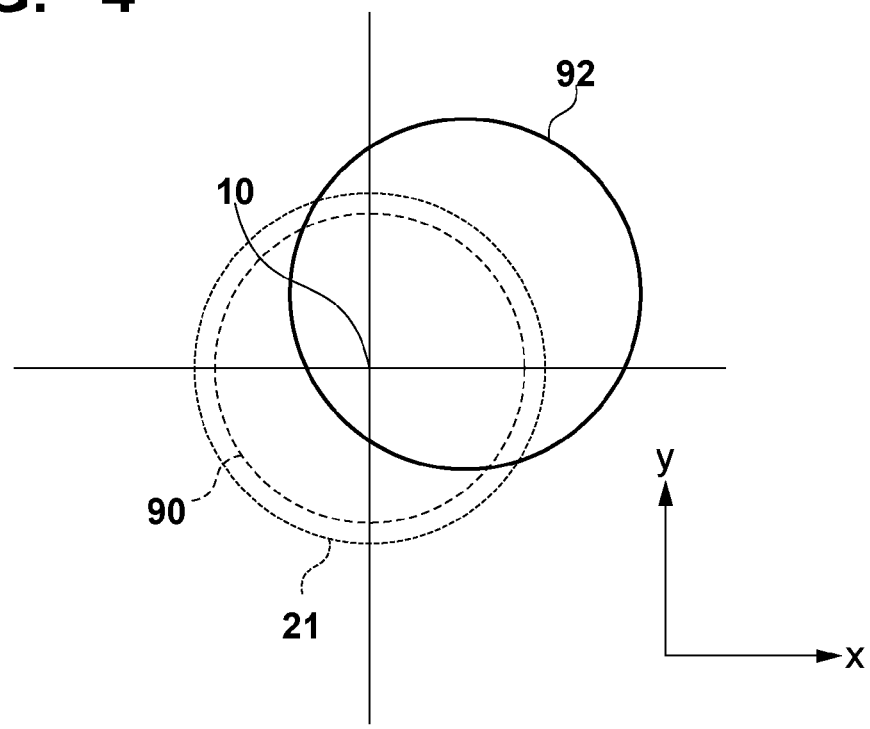
FIG. 4 is a view showing the positional relationship between illumination light on an aberration correction device and return light.

Assume that the eye 11 has moved in an x-y plane perpendicular to the optical axis (z direction) and has moved to the position of an eye 12 to be examined indicated by the solid line. Assume that at this time, the light beam diameter of the illumination light 90 is equal to or less than the diameter of a pupil 122 of the eye 12. In this case, as shown in FIG. 2, the pupil 122 is at a position shifted in a direction perpendicular to the optical axis 10 of the optical system, that is, the illumination light 90, and the light beam of the illumination light 90 is partly vignetted by the pupil 122, resulting in a decrease in the amount of illumination light reaching a retina 121. At the same time, the diameter of the spot formed on the retina increases by the amount by which the light beam is vignetted. As shown in FIG. 3, although the light beam of the illumination light 90 is vignetted, return light 92 from the retina 121 contains much scattered (diffused) light and has a spread, and hence emerges from the pupil 122 of the eye 12 as a light beam having the same diameter as the pupil diameter. However, since the position of the pupil 122 is shifted from the optical axis 10, the same shift is maintained at a position optically conjugate with the position of the pupil. FIG. 4 shows the positional relationship between the illumination light 90 and the return light 92 on the deformable mirror 2. The chief ray of the illumination light 90 indicated by the broken line coincides with the optical axis 10. The return light 92 indicated by the solid line strikes the deformable mirror 2 while shifting.

In this case, if the center of a correction effective region 21 indicated by the dotted line coincides with the optical axis 10, aberration correction is performed for the aberration of the return light 92 with a spatial shift, resulting in improper aberration correction. Consequently, the return light 92 is not properly focused at the pinhole 41, and hence the brightness or resolution of a retinal image is not improved. This phenomenon applies to the positional relationship between the pupil 122 and the illumination light 90 to which a reverse component of aberration is given by the deformable mirror 2. That is, the illumination light 90 is not focused into a desired spot diameter on the retina 121.

In addition, if the effective diameter of the overall optical system is equal to the diameter of the illumination light 90, and the correction effective region 21 of the deformable mirror 2 is equal to the effective diameter of the optical system, the return light 91 passes outside the effective diameter of the optical system. The light then strikes outside the correction effective region on the deformable mirror 2, resulting in improper wavefront correction. In addition, since the optical conjugate relationship (pupil imaging relationship) between the pupil 122, the deformable mirror 2, and the HS sensor 3 partly deteriorates, wavefront shapes at the respective positions do not coincide with each other. This makes it more difficult to perform correction.

Figure 5:
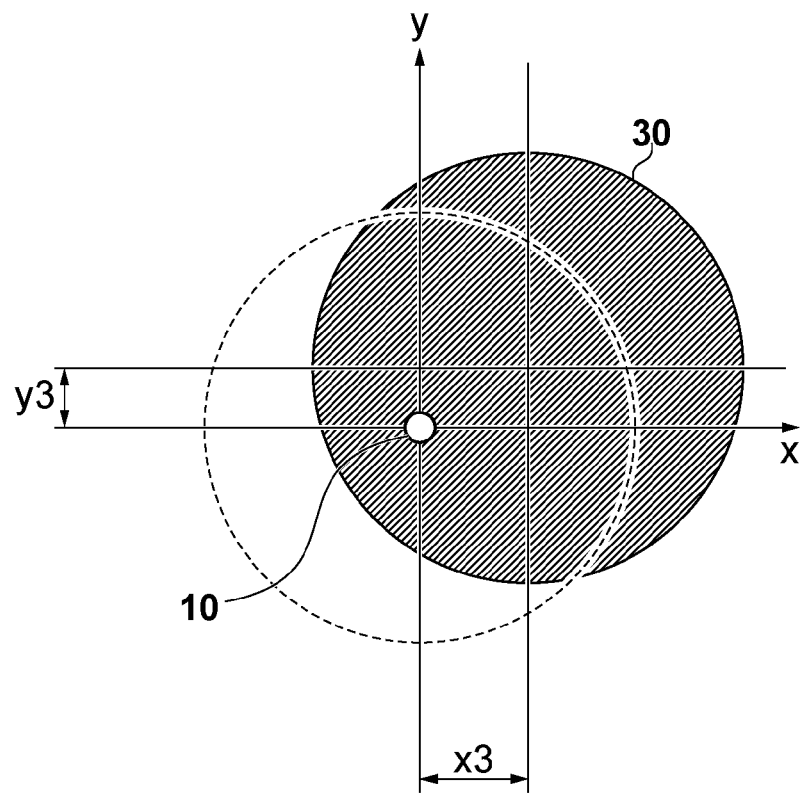
FIG. 5 is a view showing the position of return light on a wavefront detector.

This embodiment is therefore configured to detect the shift amount of the eye 12 relative to the optical axis 10 of the optical system by using the HS sensor 3 and make the correction effective region 21 on the deformable mirror 2 follow the shifted position of the return light 92. If the eye 11 has shifted from the optical axis 10 and is located at the position of the eye 12, an HS image 30 on the HS sensor 3 is also observed while being shifted from the optical axis 10, as shown in FIG. 5. Calculating central coordinates (x3, y3) of the HS image 30 will therefore obtain the coordinates of the center position of the pupil 122 of the eye to be examined as $(xp, yp)=(x3/\beta 3, y3/\beta 3)$. At the same time, since the central coordinates of the return light 92 on the deformable mirror 2 are also obtained as $(x2, y2)=(x3\cdot\beta 2/\beta 3, y3\cdot\beta 2/\beta 3)$, the central coordinates of the correction effective region 21 on the deformable mirror 2 may be determined to the same values. The position of the correction device corresponding to the shift of the eye to be examined relative to the optical axis of the illumination optical system may be determined to almost the center position of the correction effective region. The arrangement configured to detect the shift amount of the pupil 122 uses the position information of the HS image obtained by the HS sensor 3 in position detection processing according to this embodiment. However, the present invention is not limited to this, and may also provide an anterior ocular segment observation system to image the anterior ocular segment using a camera and detect the position of the eye to be examined from the position information of a pupil image as an obtained observation result.

Figure 6A:
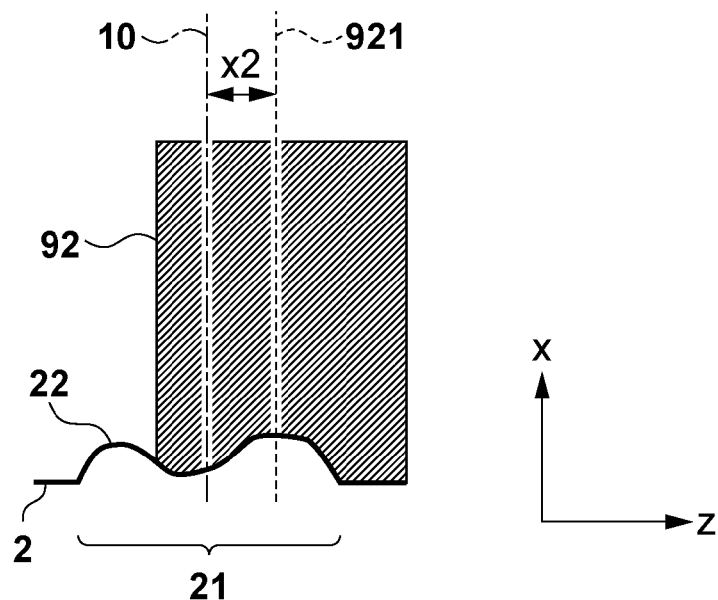
FIGS. 6A and 6B are conceptual views according to the first embodiment of the present invention.
Figure 6B:
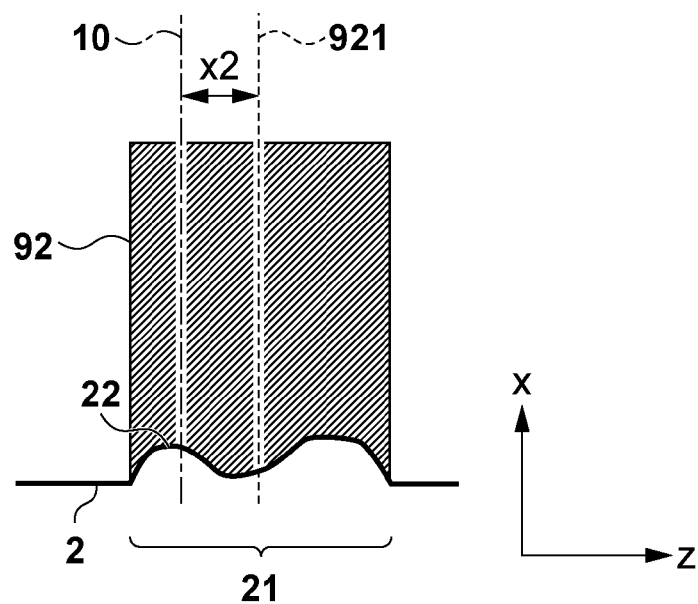

FIGS. 6A and 6B are conceptual views showing this case. Consider only an x-z plane. A chief ray 921 of the return light 92 strikes the correction effective region 21 while shifting from the optical axis (the center of the deformable mirror 2) 10 by x2. At this time, a correction shape function 22 measured and calculated by the HS sensor 3 is formed in the correction effective region 21. As shown in FIG. 6A, if the center of the correction effective region 21 remains coincident with the optical axis 10, the center does not coincide with the return light 92. In this case, as shown in FIG. 6B, the centers of the correction effective region 21 and correction shape function 22 are shifted by the value of x2 simultaneously measured and calculated by the HS sensor 3 to match the centers with the position of the chief ray 921 of the return light 92. Referring to FIG. 1, the solid line portion on the wavefront corresponds to the correction effective region 21. This properly corrects the aberration of the return light 92 without making it inconsistent with the correction effective region 21.

Consider a case in which a measured wavefront is expressed by using a Zernike polynomial. When a Zernike polynomial is used to express the aberration of the eye, each term is expressed by the following relationship between a term number, an order, and an expression:

| Term Number | Order | Expression |
|---|---|---|
| 0 | 0 | 1 |
| 1 | 1 | $2y$ |
| 2 | 1 | $2x$ |
| 3 | 2 | $2\sqrt{6} \cdot xy$ |
| 4 | 2 | $\sqrt{3}(2x^2 + 2y^2 - 1)$ |
| 5 | 2 | $\sqrt{6}(x^2 - y^2)$ |
| 6 | 3 | $\sqrt{8}(3x^2y - y^3)$ |
| 7 | 3 | $\sqrt{8}(3x^2y + 3y^2 - 2y)$ |
| 8 | 3 | $\sqrt{8}(3x^3 + 3xy^2 - 2x)$ |
| 9 | 3 | $\sqrt{8}(x^3 - 3xy^2)$ |
| 10 | 4 | . |
| 11 | 4 | . |
| 12 | 4 | . |
| . | . | . |
| . | . | . |

Each term corresponds to each aberration term of optics, and a wavefront aberration is expressed as a correction shape function $W(x, y)$ as the sum of the products between the respective terms and coefficients. Aberration correction uses the coefficient by which each term is multiplied as a parameter for feedback operation.

It is also possible to express a correction shape function $W'(x, y)$ by using these coefficients including the shift components of the pupil in addition to aberration components corresponding to the respective terms which are intrinsically included. In order to ensure the accuracy of a correction shape function, a larger number of terms are required. This requires a longer calculation time. In contrast to this, limiting the number of terms to be used will lead to a deterioration in the accuracy of a correction shape function.

In this case, $W(x-x2, y-y2)$ is used as a correction shape function formed on the deformable mirror 2 by using the value of (x2, y2) detected and calculated by the HS sensor 3. This makes it possible to accurately form a correction function with the possible smallest number of terms. This can match the return light 92 with the correction function of the correction effective region without requiring any mechanism for moving the deformable mirror itself or the like.

Consider also illumination light. In order to prevent light beam vignetting at the eye 12 shifted from the optical axis 10, the light beam diameter of the illumination light 90 may be set to the value obtained by adding the expected shift amount of the pupil 122 to the pupil diameter. In this embodiment, since the diameter of the exit pupil of the optical system is set to 12 mm, the light beam diameter of illumination light is also set to 12 mm. At this time, since the diameter of the pupil 122 is set to 6 mm, even if the pupil shifts by ±3 mm, illumination light always strikes the pupil 122 with a stable incident light intensity and a stable light beam diameter without any vignetting. Therefore, the illumination light 90 striking the eye 12 and the return light 92 always coincide with each other, each being regarded as the light beam having the marginal rays represented by the solid lines in FIG. 1.

In addition, limiting the light beam of each of the illumination light 90 and the return light 92 within the effective diameter range of the optical system will maintain the pupil imaging relationship between the pupil 122, the deformable mirror 2, and the HS sensor 3. This makes it possible to properly perform aberration correction.

In this embodiment, the light beam diameter of illumination light striking the eye 12 is determined by the diameter of the pupil 122. In this case, while aberration correction is properly performed, the larger the diameter of the pupil 122, the smaller the spot diameter on the retina. At this time, as the spot diameter decreases, the irradiation energy per area increases, and hence a higher burden is placed on the patient. For this reason, this embodiment calculates the light beam diameter of the return light 92 from an HS image as well as its position by using the HS sensor 3, and adjusts the amount of light emitted from the illumination light source 6 in accordance with the calculated value, as needed (light intensity control processing).

In addition, in this embodiment, the wavefront detection light 63 is fixed so as to strike the eye to be examined while shifting from the optical axis 10 of the optical system by about 2 mm. However, it is possible to perform follow-up control on the incident position in accordance with the detected shift amount of the eye 12. Furthermore, referring to FIG. 1, the wavefront detection light 63 strikes the eye to be examined from a position immediately before the eye. However, the light may strike the eye from a position closer to the light source than the scanner mirror 5.

As described above, this embodiment properly performs aberration correction on the deformable mirror without any spatial inconsistency between the illumination light 90 and the return light 92, thereby stably and properly forming return light into an image at the pinhole 41. In addition, the embodiment is free from a light intensity loss or an excessive increase in spot diameter due to illumination light vignetting, and can obtain a stable retinal image with proper utilization efficiency.

Second Embodiment

An SLO 101 according to the second embodiment of the present invention will be described next with reference to FIG. 7. The basic arrangement of the second embodiment and reference numerals denoting the respective units are the same as those of the first embodiment described with reference to FIG. 1. FIG. 7 shows an x-z plane. The arrangement in FIG. 7 differs from that in FIG. 1 in that the light beam diameter of illumination light 90 is set to the same diameter as the eye to be examined, that is, 6 mm, and a mirror 79 is placed between a collimator lens 71 and a half mirror 76. The illumination light 90 collimated by the collimator lens 71 is reflected by the mirror 79 at an almost right angle and propagates along the optical system after the first half mirror. In addition, the mirror 79 is placed on a mechanism which shifts reflected light from the mirror in the optical axis direction. In this embodiment, the image obtaining illumination light 90 also serves as wavefront detection light, and a mirror 77 is not a dichroic mirror but is a half mirror having a transmittance of 10% and a reflectance of 90%. In addition, the embodiment does not include the second dichroic mirror 78.

When an eye 11 to be examined is located at a position with no shift from an optical axis 10, the mirror 79 is located at a reference position (indicated by the broken line), and the illumination light 90 propagates as a light beam having the marginal rays indicated by the dotted lines and strikes the eye 11. When the eye 12 is located at a position shifted in the x direction, the mirror 79 is located at the position indicated by the solid line which is shifted by three times the shift amount of return light 92 detected by an HS sensor 3.

This method can match the illumination light 90 with a pupil 122, as needed, and can also match the return light 92 with the illumination light 90 by preventing light beam vignetting. In this case, consideration is given to only shifts in the x direction. When also performing follow-up control in the y direction, it is possible to cope with the two-dimensional shifts of the pupil 122 in the x and y directions by placing one more mirror near the mirror 79 so as to reflect illumination light in the y-z plane direction and adding a mechanism for shifting the mirror in the reflection optical axis direction. It is possible to obtain the same function as that described above by integrating the exit end of a fiber 60 and the collimator lens 71 into one unit without using the mirror 79 and providing a mechanism of shifting the unit in the x and y directions. This embodiment controls a correction effective region 21 of a deformable mirror 2 so as to always match the illumination light 90 with the return light 92 as in the first embodiment.

According to the arrangement of this embodiment, it is possible to obtain a stable image while keeping the spot diameter of illumination light on the retina constant regardless of the pupil diameter of the eye to be examined.

Third Embodiment

Figure 8:
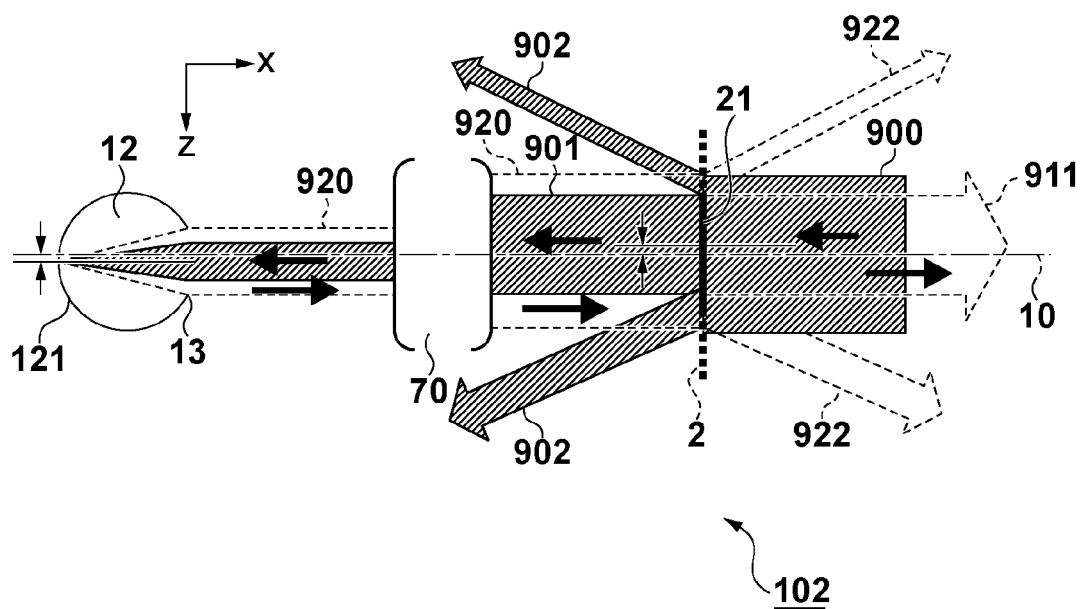
FIG. 8 is a view showing the arrangement of an adaptive optics unit according to the third embodiment of the present invention.

An adaptive optics unit 102 of a fundus imaging apparatus according to the third embodiment will be described with reference to FIG. 8. FIG. 8 shows only a portion indicating the relationship between the eye to be examined and an aberration correction device 2. The same reference numerals denote the same parts as in the first embodiment described with reference to FIG. 1. FIG. 8 shows an x-z plane. This embodiment uses a phase spatial modulator (SLM) using a liquid crystal as the aberration correction device 2. A deformable mirror is designed to change an optical path length by changing the shape of the mirror to change the spatial distance. In contrast to this, the SLM is designed to correct a wavefront by changing the refractive index of the liquid crystal so as to change the optical path length as refractive index x spatial distance. FIG. 8 shows a transmission type SLM. However, it is possible to use a reflection type SLM.

Referring to FIG. 8, a pupil 122 of an eye 12 to be examined and the SLM 2 are arranged in an optically conjugate relationship through an optical system 70. Assume that the optical system 70 includes optical systems 74 and 75 and a scanner mirror 5 in the arrangements shown in FIGS. 1 and 7. Light beams 900 and 901 indicated by the hatchings indicate illumination light, and the light beam having the marginal rays indicated by the broken lines indicates return light. The broken lines also indicate the effective diameter of the optical system. The SLM 2 has the same effective diameter as that of the optical system.

When the light beam 900 strikes the SLM 2, this apparatus modulates the phase of the light beam in accordance with a correction shape function W(x, y) detected and calculated by a wavefront detector (not shown). The light beam then strikes the optical system 70 and the pupil 122 of the eye 12. The anterior ocular segment optical system of the eye 12 then focuses the light beam on a retina 121. Return light 920 from the retina 121 emerges from the anterior ocular segment upon being aberrated by the anterior ocular segment, and strikes the SLM 2 again through the optical system 70. The light is then modulated and emerges from the SLM 2. The detector detects the light through an optical system (not shown).

In the SLM 2, the correction shape function W(x, y) is displayed within only a correction effective region 21, and the wavefront of only light, of the illumination light 900 and the return light 920, which is transmitted through this range is corrected. This embodiment sets the center of the correction effective region 21, as needed, in accordance with the shift amount of the eye 12 detected and calculated by a wavefront detector 3 as in the first and second embodiments.

Figure 9:
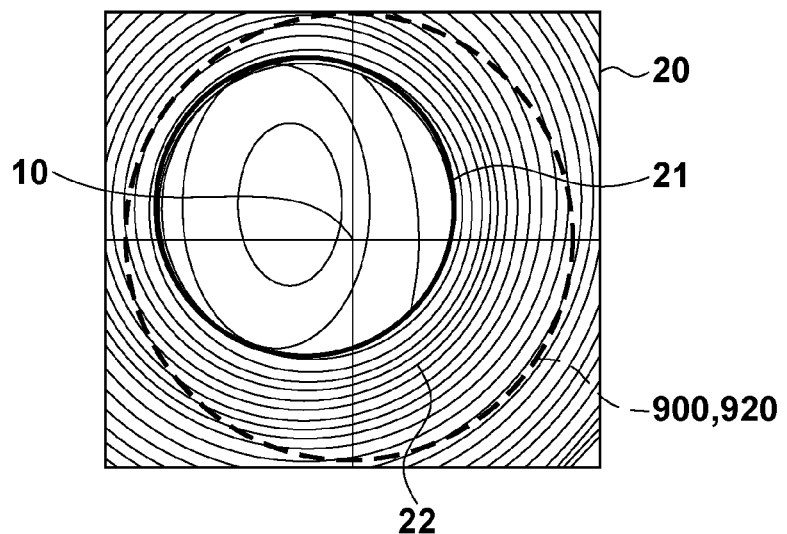
FIG. 9 is a conceptual view of an aberration correction device according to the third embodiment of the present invention.

FIG. 9 shows how modulation is performed on the SLM 2 surface. A rectangular frame 20 is the modulation driving region of the SLM 2. A center 10 is the optical axis of the optical system. A broken line 900 (920) indicates incident illumination light or return light. Reference numeral 21 denotes a correction effective region. Many curves shown in the modulation driving region 20 are a set of points at which phase modulation amounts become multiples of $2\pi$ (a correction amount represented by a wavelength unit).

In this case, modulation is performed such that a correction shape function W(x, y) is displayed in the correction effective region 21 as described above, and many concentric circles representing phase modulation amounts on a $2\pi$ basis are displayed in a region 22 outside the region 21 at small intervals with reference to the center 10. This indicates that a diffraction grating having optical power which increases in the diffracting direction is set. If modulation is properly performed (to make diffraction power become negative) such that the diffracting direction moves from the optical axis 10, light 902 transmitted through the region 22 shifts from the effective diameter of the optical system 70 and does not reach the eye 12. This also applies to return light. Light 922 transmitted through the region 22 does not pass through the subsequent optical system and is not detected by the detector.

This arrangement can keep the light beam diameter of the illumination light 901 striking the eye 12 constant and keeping the spot diameter (resolution) on the retina 121 constant without using any mechanism even with individual differences and variations in pupil diameter. This makes it possible to obtain an image with a stable brightness and resolution. In addition, setting the correction effective region 21 and illumination light intensity as needed can capture an image with a desired resolution.

The above embodiment has exemplified the SLO. It is possible to obtain the same effects as those described above by applying the present invention to, for example, an OCT or fundus camera.

According to the present invention, even if the position of the eye to be examined shifts, it is possible to perform aberration correction in accordance with the shift and stably obtain a bright image with a high resolution.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-100136 filed on Apr. 27, 2011, which is hereby incorporated by reference herein in its entirety.

The invention claimed is:

1. A fundus imaging apparatus comprising:
   a wavefront detection unit configured to detect a wavefront of return light from an eye to be examined irradiated with light through an optical system;
   a correction unit configured to correct an aberration of the return light by driving a correction effective region which is a partial region of a driving region of said correction unit based on the detected wavefront; and
   a shift unit configured to shift a position of the correction effective region within the driving region of said correction unit and in a direction perpendicular to an optical axis of said apparatus based on shift information of the pupil position of the eye,
   wherein said correction unit corrects the aberration of the return light by driving the shifted correction effective region of said correction unit based on a detection result of said wavefront detection unit.

2. The apparatus according to claim 1, wherein the shift information of the pupil position of the eye is a shift amount of a position, shifted away from the optical axis of said apparatus by movement of the pupil of the eye, of return light from the eye.

3. The apparatus according to claim 1, further comprising an observation unit configured to observe an anterior ocular segment of the eye,
   wherein the shift information of the pupil position of the eye is detected based on an observation result obtained by said observation unit.

4. The apparatus according to claim 1, wherein the shift information of the pupil position of the eye is detected based on a position of the return light applied to a detection region of said wavefront detection unit.

5. The apparatus according to claim 1, wherein said correction unit corrects light incident to the eye through the optical system and/or an aberration of return light from the eye.

6. The apparatus according to claim 1, further comprising:
   a diameter detection unit configured to detect a pupil diameter of the eye; and
   an area control unit configured to control an area of the correction effective region based on the shift information of the pupil position of the eye and the pupil diameter.

7. The apparatus according to claim 1, wherein a light beam diameter of the light is larger than a pupil diameter of the eye, and a diameter of the driving region of said wavefront detection unit and a diameter of a detection region of said correction unit are larger than the light beam diameter of the light.

8. A fundus imaging apparatus comprising:
   a light source;
   a position detection unit configured to detect shift information of a pupil of an eye to be irradiated with light from said light source;
   a wavefront detection unit configured to detect a wavefront of return light from the eye irradiated with the light;
   a correction unit configured to correct an aberration of the return light by driving a correction effective region which is a partial region of a driving region of said correction unit based on the detected wavefront; and
   a shift unit configured to shift a position of the correction effective region within the driving region of said correction unit in direction perpendicular to an optical axis of the apparatus based on the shift information detected by said position detection unit,
   wherein said correction unit corrects the aberration of the return light, based on a detection result of said wavefront detection unit, by driving the shifted correction effective region of said correction unit.

9. The apparatus according to claim 8, wherein said position detection unit includes (a) an observation unit configured to observe an anterior ocular segment of the eye and (b) detects the shift information of the eye based on an observation result obtained by said observation unit.

10. The apparatus according to claim 8, wherein said position detection unit detects the shift information of the pupil of the eye in the direction perpendicular to the optical axis of the apparatus based on a position of the return light applied to a detection region of said wavefront detection unit.

11. A method of controlling a fundus imaging apparatus, the method comprising:
    a wavefront detection step of detecting a wavefront of return light from an eye to be examined irradiated with light through an optical system;
    a correction step of correcting an aberration of the return light by driving a correction effective region which is a partial region of a driving region of a correction unit based on the detected wavefront; and
    a shift step of shifting a position of the correction effective region within the driving region of the correction unit and in a direction perpendicular to an optical axis of the apparatus based on shift information of the eye,
    wherein in said correction step, based on a detection result of said wavefront detection step, the aberration of the return light is corrected by driving the shifted correction effective region of the correction unit.

12. An apparatus comprising:
a wavefront detection unit configured to detect a wavefront of return light from an eye to be examined irradiated with light through an optical system;
a correction unit configured to correct an aberration of the return light by driving a correction effective region which is a partial region of a driving region of said correction unit based on the detected wavefront; and
a shift unit configured to shift a position of the correction effective region within the driving region of said correction unit and in a direction perpendicular to an optical axis of the apparatus so as to match the position of the correction effective region with a position of the return light on the driving region,
wherein said correction unit corrects the aberration of the return light by driving the shifted correction effective region of said correction unit based on a detection result of said wavefront detection unit.

13. The apparatus according to claim 12, wherein a position detection unit detects shift information of the return light in the direction perpendicular to the optical axis of the apparatus based on a position of the return light applied to a detection region of said wavefront detection unit.

* * * * *